United States Patent [19]

Schwindeman

[11] Patent Number: 4,659,836

[45] Date of Patent: Apr. 21, 1987

[54] IMIDAZOLIDINONE IMINES

[75] Inventor: James A. Schwindeman, Fairlawn, Ohio

[73] Assignee: PPG Industries, Inc., Pittsburgh, Pa.

[21] Appl. No.: 894,502

[22] Filed: Aug. 5, 1986

Related U.S. Application Data

[63] Continuation of Ser. No. 742,690, Jun. 10, 1985, abandoned.

[51] Int. Cl.$^4$ .............................................. C07D 413/04
[52] U.S. Cl. ...................................... 548/133; 548/245; 548/246
[58] Field of Search ......................... 548/133, 245, 246

[56] References Cited

U.S. PATENT DOCUMENTS

| | | | |
|---|---|---|---|
| 3,822,280 | 7/1974 | Moser et al. | 548/133 X |
| 4,426,527 | 1/1984 | Lavanish et al. | 71/92 X |
| 4,471,123 | 9/1984 | Varie et al. | 548/245 X |
| 4,500,343 | 2/1985 | Burow | 548/133 X |

FOREIGN PATENT DOCUMENTS 2543552 10/1984 France ................................. 548/246

OTHER PUBLICATIONS

Hofmann, K., *Imidazole and Its Derivatives*, Part I, Interscience, New York, 1953, pp. 64–65.
Williams, A., et al., *J. Chem. Soc., Perkin. Trans. 2*, 1974, pp. 1753–1759.
March, J., *Advanced Organic Chemistry*, McGraw Hill, New York, 1968, p. 683.

*Primary Examiner*—Richard A. Schwartz
*Attorney, Agent, or Firm*—Edward J. Whitfield

[57] ABSTRACT

Imidazolidinone imines are provided as well as a process for preparing same including corresponding imidazolidinone amines which compounds are useful as herbicides.

1 Claim, No Drawings

IMIDAZOLIDINONE IMINES

This application is a continuation of application Ser. No. 742,670, filed June 10, 1985, now abandoned.

FIELD OF THE INVENTION

This invention relates to imidazolidinone imines and to a process for preparing imidazolidinone imines and amines which compounds are useful as herbicides.

DESCRIPTION OF THE INVENTION

This invention relates to a process for preparing herbicidally active imidazolidinone amine compounds represented by the Formula I:

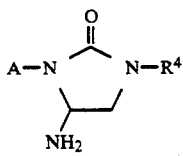

wherein A is

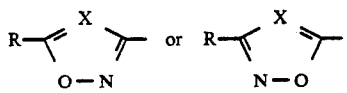

wherein:
X is CH or N;
R is up to $C_6$ alkyl, haloalkyl or cycloalkyl, up to $C_5$ alkenyl or alkynyl, $-R^2-O-R^3$ or $-R^2-S-R^3$ wherein $R^2$ is up to $C_6$ alkylene and $R^3$ is up to $C_6$ alkyl or optionally substituted phenyl or benzyl; and $R^4$ is up to $C_3$ alkyl or allyl.

The process of this invention involves reacting a 3- (or 5-) isocyanato isoxazole of the formula or a 3- (or 5-) isocyanato oxadiazole of the Formula II:

wherein A is as previously defined, with a substituted aminoacetonitrile of the Formula III:

wherein $R^4$ is as previously defined, to obtain a novel imidazolidinone 4-imine of the Formula IV:

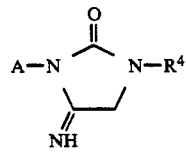

wherein A and $R^4$ are as previously defined.

The imine of Formula IV is then hydrogenated to obtain a Formula I compound.

More particularly, equivalent amounts of the Formula II and Formula III compounds are reacted at up to reflux temperature typically in the presence of an inert solvent and a tertiary amine catalyst, for a time sufficient to assure complete conversion of starting material. Some suitable solvents include toluene, tetrahydrofuran, chloroform, benzene or the like. Triethylamine, tributylamine, diethylaniline and the like are exemplary of suitable catalysts.

The novel Formula IV compound thus obtained is then hydrogenated to obtain the desired Formula I compound. Hydrogenation may be effected by contacting the Formula IV compound with gaseous hydrogen in the presence of a suitable solvent and a suitable catalyst. Exemplary solvents include benzene, ethyl acetate, ethanol, glacial acetic acid or the like. Palladium, palladium on carbon or metallic sodium are exemplary of suitable catalysts. Hydrogenation could also be effected by electrochemical reduction.

The process of this invention is illustrated as follows.

(a) To a flask provided with a reflux condenser a magnetic stirring bar and a drying tube is charged with 5-(t-butyl)-3-isocyanato isoxazole, dry toluene and a catalytic amount of dry triethylamine. To this stirred mixture is added an equivalent amount of methaminoacetonitrile. The reaction mixture is then heated to reflux and maintained at reflux until HPLC analysis indicates complete consumption of starting material. The reaction mixture is then cooled, transferred to a separatory funnel, diluted with ethyl acetate and washed with saturated aqueous sodium bicarbonate and saturated aqueous sodium chloride solutions. The organic layer is dried over anhydrous magnesium sulfate, filtered and concentrated in vacuo affording 3-[5-(t-butyl)-3-isoxazolyl]-1-methyl-4-imino-2-imidazolidinone.

(b) The 4-imino compound prepared as described in paragraph (a) is charged to a Parr hydrogenation bottle along with glacial acetic acid and a catalytic amount of 10 percent palladium on carbon hydrogenation catalyst. The bottle is charged with hydrogen and rocked in a Parr hydrogenation apparatus until TLC analysis indicates completeness of reaction. The bottle is then flushed with air, the catalyst removed by filtration and the reaction mixture is concentrated in vacuo to remove the acetic acid solvent. The residue is then dissolved in chloroform, dried over anhydrous magnesium sulfate, filtered and concentrated in vacuo to afford the desired product, 3-[5-(t-butyl)-3-isoxazolyl]-1-methyl-4-amino-2-imidazolidinone.

Preparation of a particular Formula I and Formula IV compound is illustrated by the foregoing and it is to be understood that other Formula I and Formula IV compounds can be readily prepared using the process of this invention simply by varying the choice of starting materials.

The Formula I compounds prepared by the process of this invention are useful as herbicides and are described in U.S. Pat. No. 4,426,527 and copending, commonly assigned U.S. application Ser. No. 606,810 filed May 3, 1984, the teachings of which are incorporated by reference herein respecting the structure and utility of said compounds.

I claim:
1. A compound of the formula:

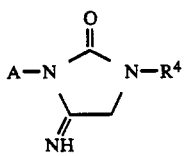

wherein A is

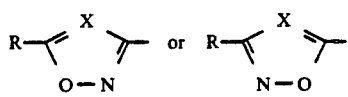
wherein
X is CH or N;
R is up to $C_6$ alkyl, haloalkyl or cycloalkyl, up to $C_5$ alkenyl or alkynyl, $-R^2-O-R^3$ or $-R^2S-R^3$ wherein $R^2$ is up to $C_6$ alkylene and $R^3$ is up to $C_6$ alkyl, phenyl or benzyl; and $R^4$ is up to $C_3$ alkyl or allyl.
* * * * *